United States Patent [19]

Rishpon et al.

[11] Patent Number: 5,147,781
[45] Date of Patent: Sep. 15, 1992

[54] ENZYME ELECTRODE AND ASSAY FOR DETERMINING LDH5

[76] Inventors: Judith Rishpon, Meonot Wolfson B, Weizmann Institute, Rehovot; Ilana Rosen, 74 Krinitzi Street, Ramat Gan, both of Israel; Zeev Hollander, 954 Celia Dr., Palo Alto, Calif. 94303

[21] Appl. No.: 20,946

[22] Filed: Mar. 2, 1987

[30] Foreign Application Priority Data

Mar. 4, 1986 [IL] Israel .......................... 78034

[51] Int. Cl.$^5$ ................. G01N 33/573; G01N 33/577
[52] U.S. Cl. ..................... 435/7.4; 435/817; 435/291; 204/1.11; 204/403
[58] Field of Search ............. 435/7, 26, 817, 291, 435/7.4; 436/527; 204/1 T, 403, 1.11

[56] References Cited

U.S. PATENT DOCUMENTS

| | | | |
|---|---|---|---|
| 4,224,125 | 9/1980 | Nakamura et al. | 204/195 B |
| 4,224,406 | 9/1980 | Gomez et al. | 435/7 |
| 4,321,123 | 3/1982 | Nakamura et al. | 204/195 B |
| 4,444,878 | 4/1984 | Paulus | 435/7 |
| 4,619,754 | 10/1986 | Niki et al. | 204/290 R |

OTHER PUBLICATIONS

Kenett, J. of Immunoassay, 9(1): 37–49, "Quantitative ELISA For Human Lactate Dehydrogenase Isoenzyme 5" (1988).

*Primary Examiner*—Esther L. Kepplinger
*Attorney, Agent, or Firm*—Browdy and Neimark

[57] ABSTRACT

The invention relates to an assay for the determination of the enzyme lactate dehydrogenase-5 (LDH5) and to a biosensor for such quantitative determination.

The assay is based on the interaction of this enzyme with the substrate lactic acid and nicotine-amine adenine dinucleotide (NAD) to yield pyruvic acid and the reduction product of NAD.

Anti-LDH5 antibody is bound to a suitable glassy carbon electrode, this is contacted with the substrate containing LDH5, rinsed, inserted into a NAD solution, connected to an amperometric system, lactic acid is added and the current changes are measured, which are indicative of the quantity of LDH-5.

9 Claims, 3 Drawing Sheets

Anti LDH5 electrode response to different lactic acid concentrations.
△ + ▫   (upper curves)
1. △    after 1st incubation with LDH5
2. +    second measurement after the 1st incubation
3. ▫    after removal of the antigen and reincubation with LDH5
◇ ▽ ✗   (lower curves)
4. ✗    after removal of the antigen
5. ▽    after incubation with LDH1
6. ◇    no antibody on the electrode; after incubation with LDH5

ENZYME ELECTRODE AND ASSAY FOR DETERMINING LDH5

FIELD OF THE INVENTION

There is provided a highly sensitive assay for the quantitative determination of the various types of LDH, especially in biological fluids.

There is further provided an enzyme electrode for such assays. Such electrodes comprise a suitable substrate (glassy carbon) to which there is attached a specific antibody, corresponding to the LDH type to be determined.

A preferred assay relates to the determination of LDH5. Another corresponding assay relates to the determination of LDH1. The only difference is the specific type of anti-LDH-antibodies bonded to the glassy carbon electrode.

There is further provided an amperometric electrochemical system which provides for convenient and high-sensitivity measurements of the above enzyme types.

According to yet another embodiment of the invention, there can be attached to the electrode the LDH enzyme type, which serves as antigen, and the solution will contain a certain quantity of anti-LDH antibodies. The substrates and mediators used are set out in detail hereinafter.

BACKGROUND OF THE INVENTION

Qualitative and especially quantitative antigens and antibody measurements are of importance in clinical chemistry, physiology, and modern biotechnology. There exists an expanding interest in developing convenient sensitive nonisotopic labeled immunoassays. Among these, immunoassays appear to be oractical. In most such assays ultimate measurement is by optical methods.

Electrochemical determination offers two practical advantages:
1. They use relatively inexpensive and simple instruments.
2. They are capable of making measurements even in highly turbid systems.

Considerable efforts have been made to develop membrane electrode sensors for antigen and antibody measurements. Antibodies were immobilized on gelatin membranes which were attached to an oxygen electrode. In such devices specific antibodies are immobilized onto a membrane and are applied in a solid phase "sandwich" procedure.

According to the invention described herein the antibodies or antigens are bound directly to an electrically conductive electrode. Together with an amperometric or other electro-chemical system, high sensitivity and reproducibility of measurements of antigens and antibodies, respectively, can be obtained.

The determination of LDH5 (which is part of the entire LDH content) in sera is of clinical significance as the level of LDH5 is indicative of liver functions, an increased content indicating liver malfunction. In a similar manner LDH1 can be determined, and this is of value in tests for coronary infarcts and the like.

SUMMARY OF THE INVENTION

There is provided a novel biosensor for the determination of various types of LDH. More specifically, there &s provided a novel immunoelectrochemical sensor which comprises an electrode to which there are chemically or otherwise bonded antibody molecules of the anti-LDH type. The preferred mode of bonding is a covalent one. There is further provided an analytical electrochemical amperometric system for the detection and quantitation of LDH5 and LDH1.

The novel biosensors utilize the high sensitivity of modern electrochemical methods and the high selectivity and specificity of antibody action, and in particular that of monoclonal antibodies. When an electrode of the invention, to which there is bonded a specific type of anti-LDH antibodies, is contacted with a solution which contains the corresponding antigen LDH (any specific type), which is adapted to interact with this specific type of antibodies, the antigen is selectively adsorbed from such solution to said electrode surface. There is obtained an "enzymatic electrode" the activity of which is directly proportional to the quantity of bond antigen, which is indicative of the concentration of such antigen in the solution which is being assayed. When this enzymatic electrode is in contact with a solution containing the specific antigen not bound to the redox enzyme the activity of the electrode will decrease according to the concentration of the free antigen in the solution, via competition effects.

A further technique comprises covalently bonding to the electrode, such as a glassy carbon, suitable anti-LDH-antibodies, inserting the sensor into a solution of this conjugate and free protein, establishing the current curve which is indicative of the ratio of the protein conjugate to the free protein.

The assay of this invention, and the enzyme electrode for use in such assay, are based on the enzymatic reaction of the enzyme lactate dehydrogenase (LDH) which interacts with the substrate lactic acid and nicotinamide adenine dinucleotide (NAD), which yields the reduction product of NAD, which is designated as NADH.

The sensitivity of the assay is increased by carrying out the electrochemical measurement in the presence of the mediator PMS (phenazine metasulfate), which by interaction with NADH is converted to PMSH (the reduction product), which makes possible measurements in the nanogram/ml range.

The assays can be used in clinical tests and in biochemical research and production. Amongst diagnostic purposes there may be mentioned determinations of different LDH isoenzymes, the ratio of which changes in pathological situations such as heart or liver diseases. Thus, biosensors of the invention with monoclonal anti-LDH-antibodies bound to glassy carbon, can be used for the quantitative determination of this enzyme, providing rapid and convenient means for the diagnosis of patient condition undergoing a certain type of heart attack and liver diseases.

The electrodes used according to the present invention are preferably glassy carbon rods embedded in a Teflon-housing so as to expose a single disk of the glassy carbon.

The antibodies are chemically bound to such electrodes as follows: The first step is an activation of the glassy-carbon electrode by anodic oxidation by passing 20 miliampere for 10 seconds in a solution containing 10% $HNO_3$ and 2.5% $K_2Cr_2O_7$. After this, a droplet of a mixture containing 40 microgram/ml 1-ethyl-3-(3-dimethylaminopropyl)carbodiimide hydrochloride and 40 microgram/ml antibody in a phosphate buffer, 0.02M, pH 6 was carefully spread on the electrode surface and the electrode was allowed to dry in air for a couple of hours, and was then ready for use.

The antigens were bound to the antibody electrode by immersing the electrode in a solution containing the antigen and incubating the system for 1 hour.

The antigen could be completely removed from the antibody electrode by immersing the electrode in a solution containing glycine buffer of pH 2.2. After that, the electrode could be used again and react with a new sample of the antigen. This procedure could be repeated numerous times.

The detection system comprises amperometric detection of NADH using a carbon-disk electrode. The electrode potential used was 0.7 V. When under the same conditions phenazine metasulfate (PMS) is added, the sensitivity of the assay, especially at lower concentrations, is substantially increased. The PMS is advantageously at a 2 mM concentration. During measurements the potential of the electrode can be decreased from about 0.7 V to about 0.13 V, and this is advantageous with determination of LDH5 in serum, where higher voltages are apt to cause side-effects.

The results according to the assay of the present invention versus results obtained by electrophoresis are set out in Table 1. In this Table ECH designates the electrochemical method of this invention and EPH designates electrophoresis.

The anti-LDH5 antibodies (monoclonal) used in some of the tests of the present invention was purchased from Sigma Chemicals It is of the IgG$_1$ type and designates as 2/66 antibodies.

| LDH5 Determination in Serums | | | |
|---|---|---|---|
| Serum # | % LDH5 ECH | % LDH5 EPH | Total LDH (u/L) |
| 1762 | 11.4 | 11.9 | 157 |
| #1 | 17.8 | 16.6 | 226 |
| 3794 | 64 | 55 | 211 |
| 3572 | 45 | 62 | 855 |
| 3768 | 53 | 48 | 988 |

BRIEF DESCRIPTION OF THE DRAWINGS

The invention is illustrated with reference to the enclosed Figures, which are diagrams of results obtained and in which.

EXAMPLE 1

Detection and Determination of LDH5

Figure 1:
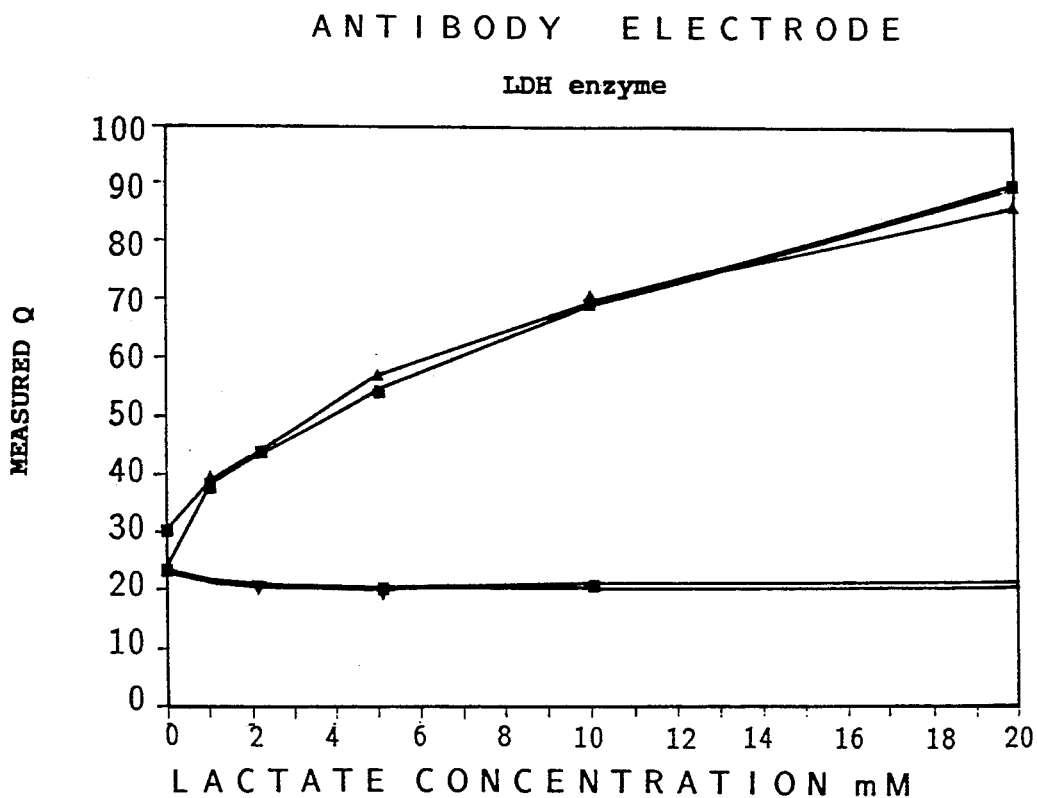
FIG. 1 illustrates the response of an Anti-LDH5 electrode to different concentrations of lactic acids.
Figure 2:
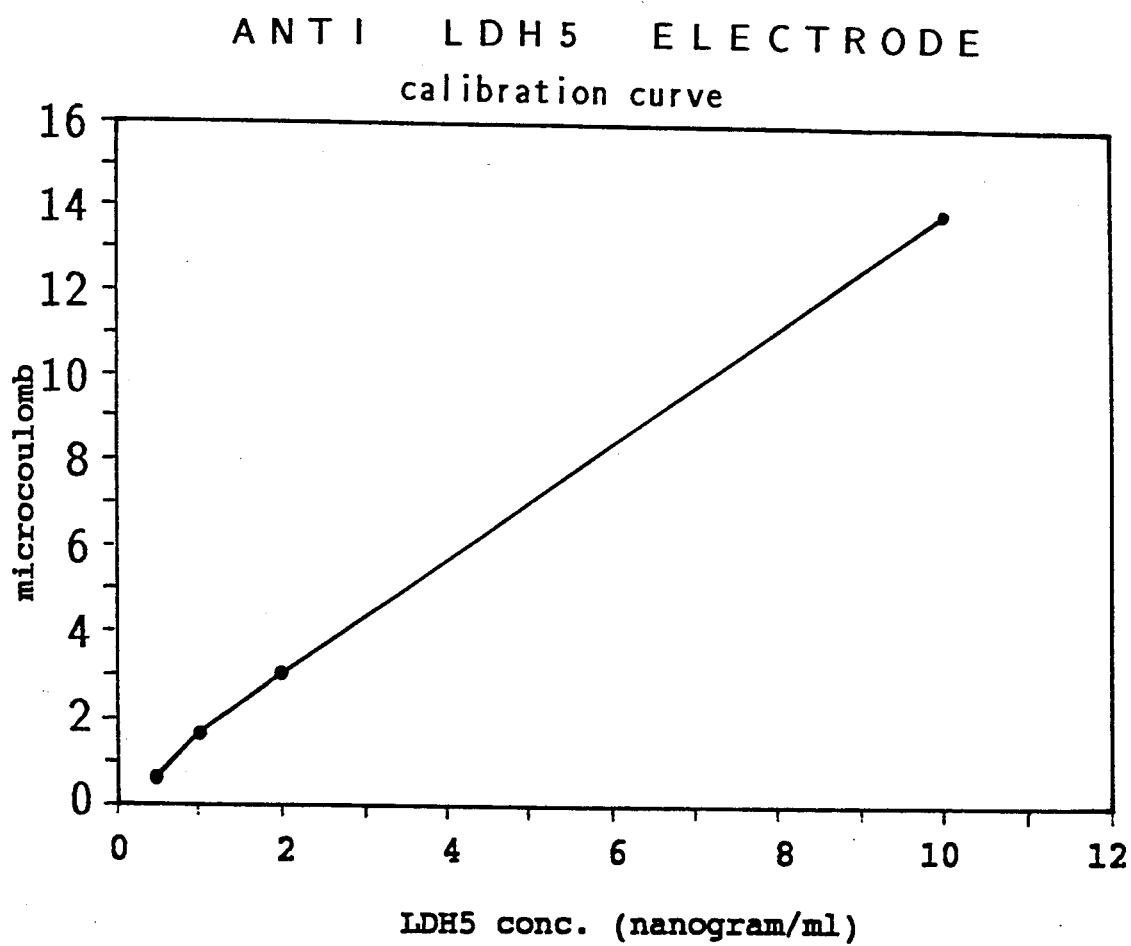
FIG. 2 is a calibration of a run according to Example 1, but with added PMS (2 mM) which makes possible quantitation in the nanogram range.
Figure 3:
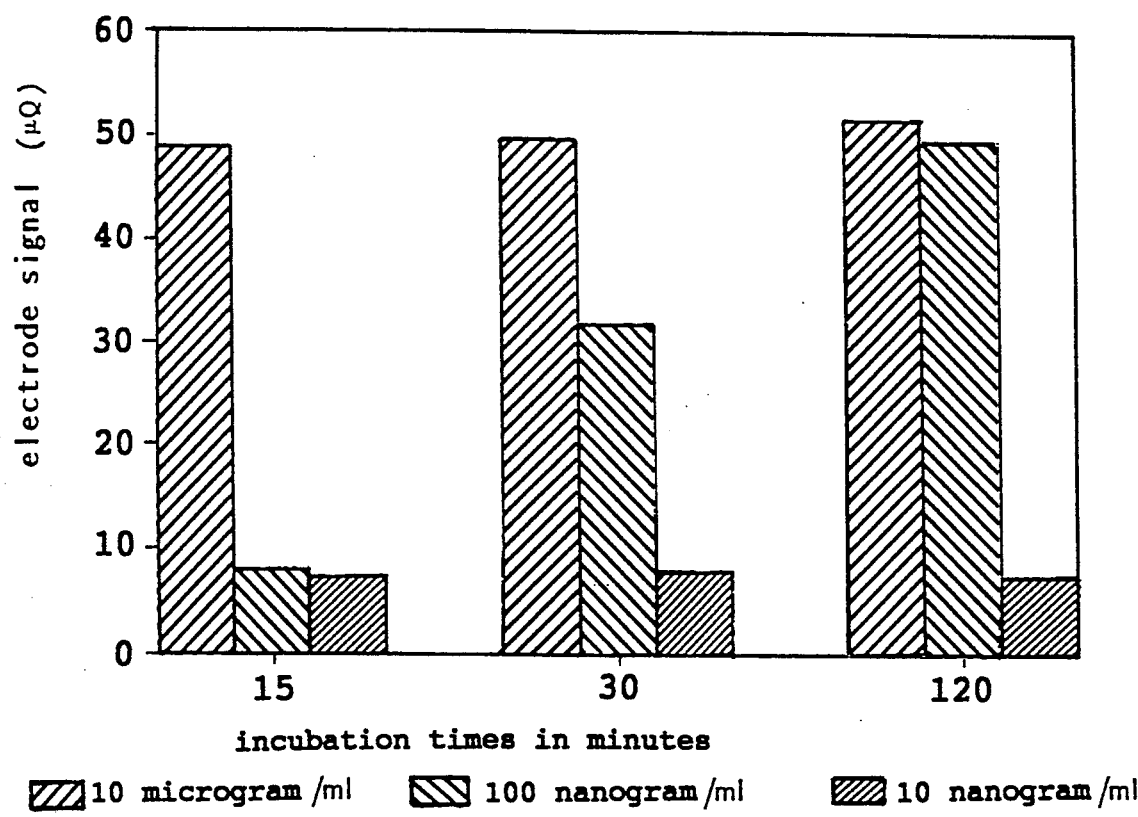
FIG. 3 illustrates the response of an Anti-LDH5 electrode after incubation with different concentrations of LDH5.

Monoclonal antibodies, namely Anti-LDH5 antibodies, were covalently bound to a glassy carbon electrode. The quantity of the antibodies bound was $200 \times 10^{-9}$ grams. When the thus produced electrode, with the monoclonal antibodies bound to its surface, was inserted into a solution containing LDH5 and incubated in such solution for 1 hour at a temperature of about 20° C., this enzyme was selectively adsorbed to the electrode surface. The electrode was then rinsed and inserted in a solution containing NAD 0.5 to 5mM at pH 9.0. By employing a potentiostatic electrochemical system, addition of sodium lactate produced an increase in the current signal which was proportional to the amount of lactic acid added and the amount of adsorbed antigen. It was possible to determine an antigen concentration in the range of about $10^{-8}$ to $10^{-4}$ g/ml.

In an analogous manner, there can be bound antigens to the surface of the glassy carbon electrode, and such glassy carbon electrodes can be used in an analogous manner to determine the corresponding antibodies. The above description is by way of illustration only and various changes and modifications can be resorted to without departing from the invention.

We claim:

1. A biosensor for the quantitative determination of enzyme LDH5 in biological fluids, comprising a glassy carbon electrode having anti-LDH5 directly bound thereto, said bound anti-LDH5 being capable of binding LDH5 in such a manner that LDH5 bound to said anti-LDH5 remains capable thereafter of specifically binding both lactic acid and NAD.

2. A biosensor according to claim 1, where the bound anti-LDH5 is a monoclonal antibody.

3. A biosensor according to claim 1, where the anti-LDH5 is covalently linked to the surface of the electrode.

4. A biosensor according to claim 1, where the glassy carbon electrode comprises a glassy carbon disk.

5. A biosensor according to claim 1, where the glassy carbon electrode comprises a rod of this material embedded in an inert housing, exposing only a portion of the glassy carbon.

6. A biosensor according to claim 3, where the bonding is via a carbodiimide.

7. As assay for the quantitative determination of LDH5, which comprises inserting a biosensor comprising a glassy carbon electrode having anti-LDH5 directly bound thereto, said bound anti-LDH5 being capable of binding LDH5 in such a manner that LDH5 bound to said anti-LDH5 remains capable thereafter of specifically binding to lactic acid and NAD, into a solution containing the LDH5 which is the antigen to be determined, incubating said biosensor in said solution, removing and rinsing the biosensor, inserting same into a solution of NAD, connecting with an amperometric system, adding lactic acid and measuring the current change.

8. An assay of claim 7, where phenazine metasulfate is added to the reaction system before carrying out the amperometric determination.

9. An assay according to claim 7, where the anti-LDH5 bonded to the glassy carbon is an IgG, monoclonal antibody.

* * * * *